United States Patent [19]
Adams

[11] Patent Number: 5,919,211
[45] Date of Patent: Jul. 6, 1999

[54] ICD POWER SOURCE USING MULTIPLE SINGLE USE BATTERIES

[76] Inventor: Theodore P. Adams, 4618 Edgebrook Pl., Edina, Minn. 55424

[21] Appl. No.: 08/884,214

[22] Filed: Jun. 27, 1997

Related U.S. Application Data

[XX .
[60] Provisional application No. 60/020,628, Jun. 27, 1996.
[51] Int. Cl.[6] .................................................. A61N 1/39
[52] U.S. Cl. .................................................. 607/5
[58] Field of Search .................... 607/4, 5, 9, 34, 607/35

[56] References Cited

U.S. PATENT DOCUMENTS

| | | |
|---|---|---|
| 4,323,075 | 4/1982 | Langer ........................................ 607/5 |
| 5,372,605 | 12/1994 | Adams et al. . |
| 5,383,907 | 1/1995 | Kroll . |
| 5,405,363 | 4/1995 | Kroll et al. ................................. 607/5 |
| 5,407,444 | 4/1995 | Kroll . |
| 5,439,482 | 8/1995 | Adams et al. . |
| 5,620,464 | 4/1997 | Kroll et al. . |

*Primary Examiner*—William E. Kamm
*Assistant Examiner*—George R. Evanisko
*Attorney, Agent, or Firm*—Brad Pedersen

[57] ABSTRACT

An implantable cardioverter defibrillator optimized for prophylactic use. An improved power system uses multiple, single use, short duration, battery cells for countershocks.

7 Claims, 3 Drawing Sheets

ICD POWER SOURCE USING MULTIPLE SINGLE USE BATTERIES

CROSS-REFERENCE TO RELATED APPLICATIONS

This application claims the benefit under 35 U.S.C. §119 (e) of co-pending provisional application Ser. No. 60/020,628, filed Jun. 27, 1996.

BACKGROUND OF THE INVENTION

1. Field of the Invention

The present invention relates, generally, to medical devices. More particularly, the invention relates to implantable cardioverter defibrillators (ICDs).

2. Background Information

In the past, various ICD devices and methods have been used or proposed. However, these devices and methods have significant limitations and shortcomings. Existing ICD's are primarily designed for chronic applications in that they produce enough shocks to treat a chronic condition wherein the patient is expected to have numerous episodes of sudden cardiac death (SCD) over an extended period. Typical defibrillators are capable of delivering from 150 to 350 full output shocks of 27 to 40 joules each (depending on the model and manufacturer). In order to deliver that many high energy shocks, the device must have sufficient battery capacity to cover the required delivered energy as well as system losses (about 30% is lost in the DC to DC converter). This necessarily adds bulk and weight to the device.

Presently, most patients undergoing ICD implantation have exhibited at least one episode of fibrillation (SCI) and survived due for example to early CPR, trans-chest defibrillation and other care. Since one episode is typically a clear indication of high risk of having another one, an ICD is indicated. Other patients exhibit very early indications for being at high risk for SCD and an ICD is implanted prophylactically. Overall, about 40% of patients who have ICD's implanted do not have another episode during the next four years. However, these patients still need protection and typically another ICD must be implanted after the battery dies in three to five years, even though no shocks are delivered by the device.

Patients who are not shocked by their ICD have unnecessarily had a large device capable of hundreds of shocks implanted. Large devices are uncomfortable and present an increased risk of infections, erosions, and certain psychological problems. A smaller device with a smaller battery (and possibly fewer functions) would serve these patients better. Such a device would have only a sufficient number of shocks available to save the patient from initial SCD episodes, whereupon the patient would immediately have a larger device with more shock capacity implanted. This type of device would be implanted in those patients who were considered at high risk, but have not yet had an episode (and may never have one) and in patients who have had a conventional large device which needs replacement, but who have not had a shock during the last several years. The concept of a prophylactic ICD is disclosed in U.S. Pat. No. 5,439,482.

It may seem obvious to a casual observer that to make a device with fewer shocks, one only need to use a smaller battery. That has not been the case, however, owing to other requirements of the battery. The battery must be capable of charging the output capacitor to its maximum output (27 to 40 joules) in a period of 6 to 10 seconds after detection of fibrillation. This typically requires from 0.7 to 1.0 amp of current during the charging period. With conventional batteries used in ICD's, Lithium Vanadium Pentoxide9 for example, the minimum size battery that meets the charging criteria has sufficient capacity for about 150 or more shocks. Thus, it has not been possible to make a limited shock device with a small battery. Virtually every battery's chemistry has this capacity/power relationship.

Accordingly, it is an object of the present invention to provide an improved ICD which overcomes the limitations and shortcomings of the prior art, particularly those related to the limitations of prior art battery systems.

BRIEF SUMMARY OF THE INVENTION

The present invention provides an improved ICD, primarily for prophylactic use.

The features, benefits and objects of this invention will become clear to those skilled in the art by reference to the following description and drawings.

DETAILED DESCRIPTION

Figure 1:
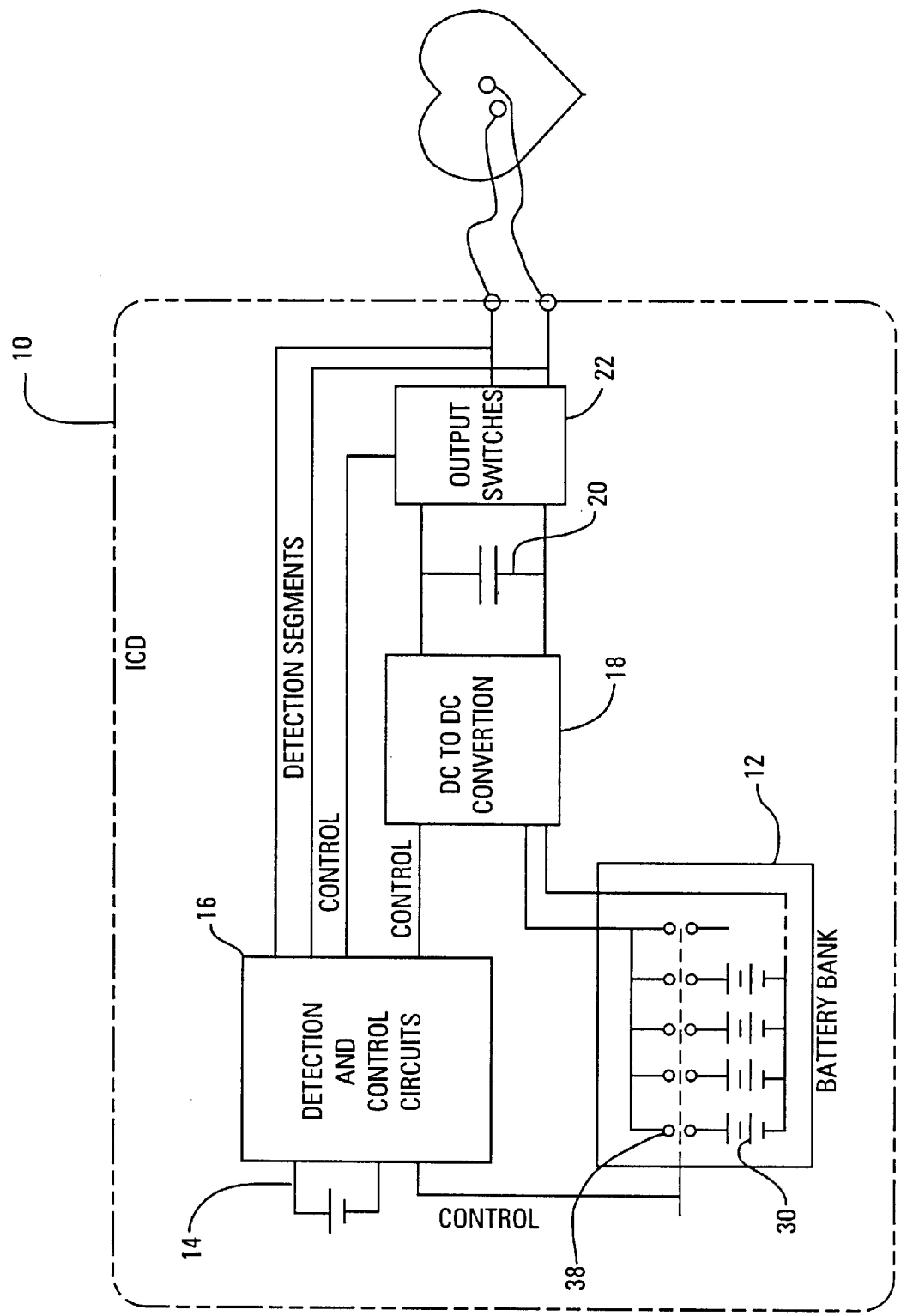
FIG. 1 is a schematic diagram of the ICD of the present invention.

Referring to FIG. 1, an example of the preferred embodiment of the present invention is illustrated. For purposes of describing the present invention, a detailed understanding of the design and operation of an implantable cardioverter defibrillator (ICD) is assumed and is not necessary to understand the present invention. For a detailed description of the general background and operation of an ICD reference is made to U.S. Pat. No. 5,405,363. The major structural and functional components of an ICD 10 in accordance with the present invention comprise a high power output battery bank 12, a low power output battery 14, detection and control circuitry 16, a DC to DC converter 18, a high voltage capacitor system 20, and an output switching network 22. The interconnection of the these components is as shown in FIG. 1.

The preferred embodiment of the details of the connection and operation of the high power output battery 12 and the low power output battery 14 are described in U.S. Pat. Nos. 5,372,605, 5,383,907, 5,407,444 and 5,620,464, the disclosure of each of these patents being incorporated by reference herein. As in these patents, the low power output battery 14 is used to power the monitoring and pacing circuitry and the high power output battery 12 is used to supply the high energy output necessary for powering the converter 18 in order to charge the capacitor system 20 so as to deliver an electrical countershock. The low power output battery 14 is preferably of LiI chemistry, such as those used in cardiac pacemakers, although other lower power output batteries could also be used. Unlike the high power output batteries described in these patents, the high power output battery 12 of the present invention is constructed of a bank of multiple small single use battery cells 30, preferably a thermal battery, such as a pyrotechnically initiated molten salt primary reserve battery.

Figure 2:
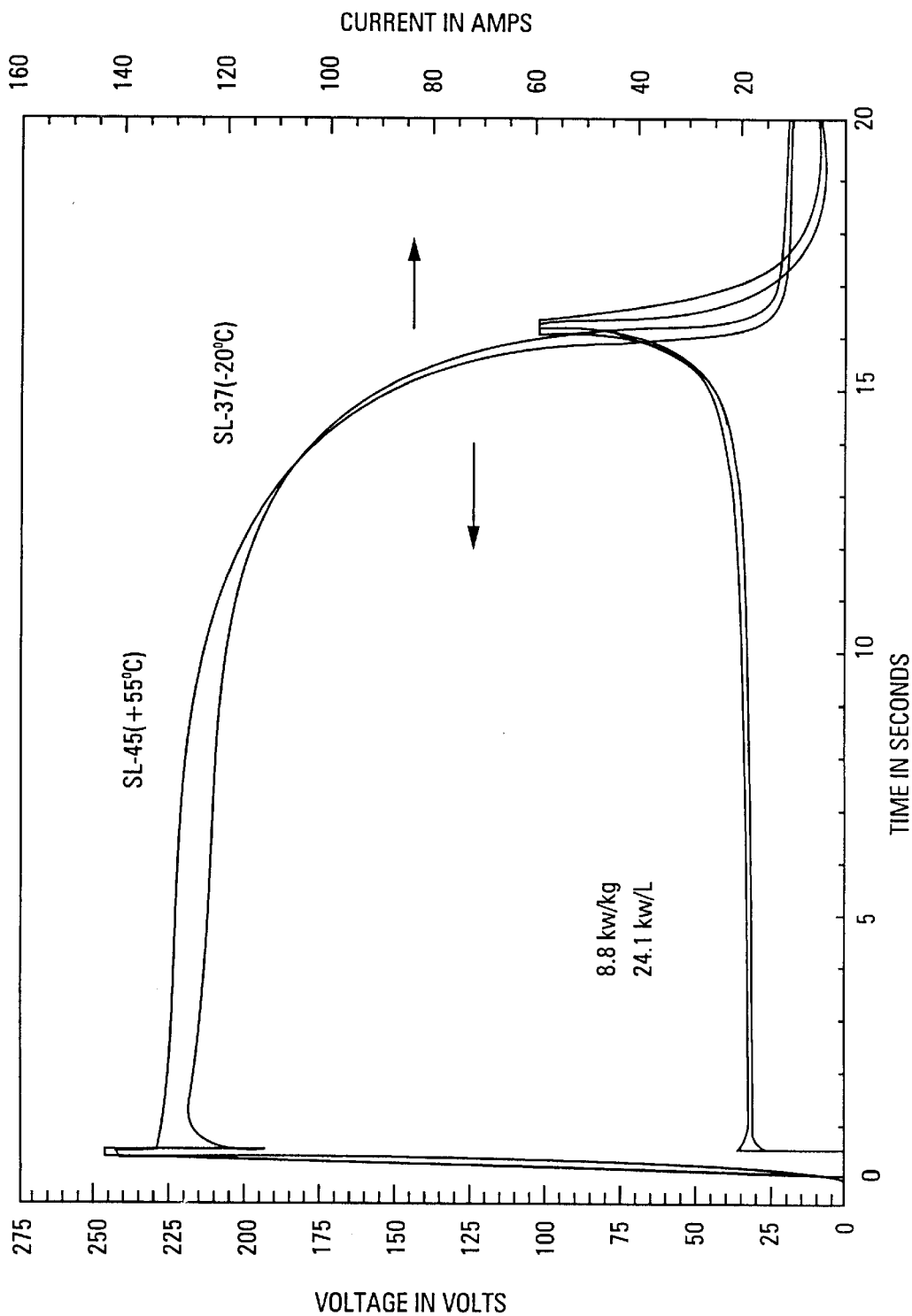
FIG. 2 is a graphical representation of the discharge characteristics of a thermal battery cell.
Figure 3:
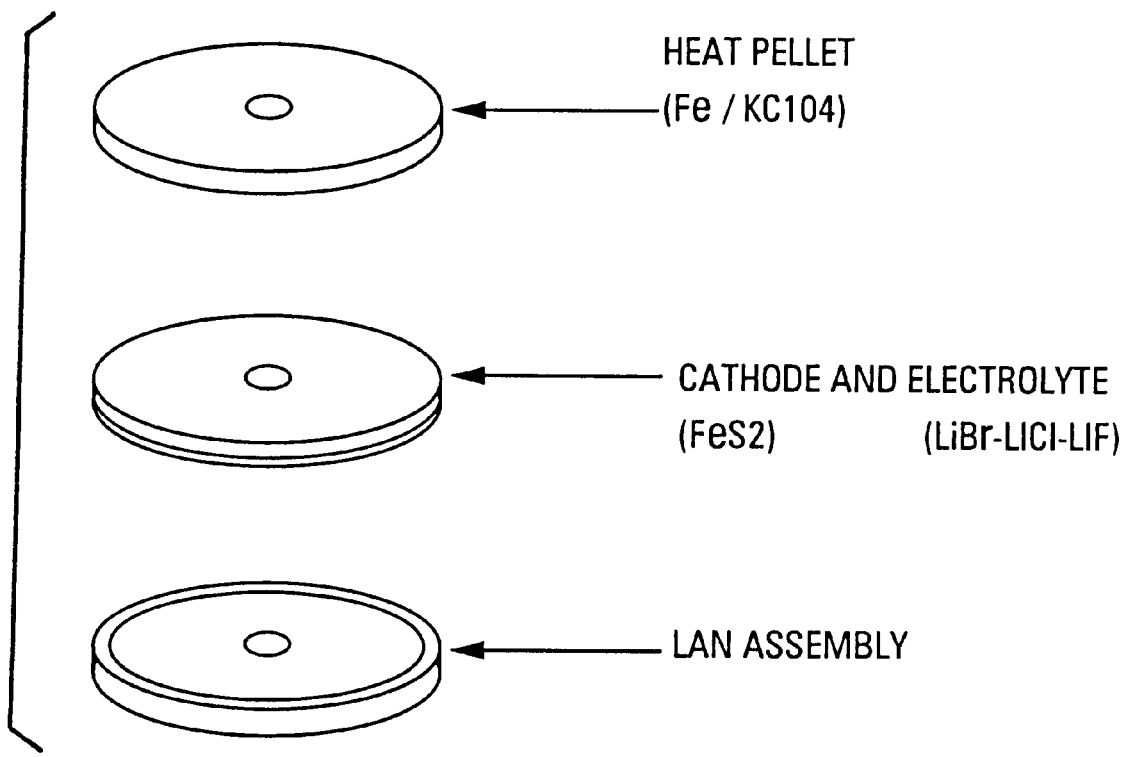
FIG. 3 is a cutaway view of the construction of the thermal batter cell.

Thermal batteries have not heretofore been used in medical devices. These types of batteries were developed for very specialized military applications and have the property of having very high energy densities. When activated, the thermal batteries are heated to a very high temperature (400 to 500 degrees Celsius) to enable the batteries to deliver extraordinarily high currents for a short period of time. The current capacity is limited by the surface area of the cell components. A graphical depiction of the discharge characteristics of a typical thermal battery cell 30 is shown in FIG. 2. FIG. 3 shows a cutaway view of the construction of a typical thermal battery cell 30, consisting of a heat pellet layer 32 ($Fe/KCLO_4$), a cathode ($FeS_2$) and electrolyte layer (LiBr, LiCl, LiF) 34 and an anode layer 36 (LAN). It will be noted that the overall dimensions of the thermal battery cell 30 are very small and allow for construction of multiple cells in a stacked construction configuration. The cell described in this embodiment is manufactured by SAFT R&D center. Additional information about such thermal battery cells is available over the Internet at "www.bmpcoe.org/knowhow/3676/81.html". The preferred configuration for the thermal battery cells 30 is such that they are capable of maintaining their energy output for only about 10 seconds, limited by the heat source capacity and chemical capacity of the cell. Because of the high temperatures generated by the battery cells 30, it may also be necessary to provide for a heat sink arrangement within the internal construction of the ICD, such as part of an internal liner or the like, to effectively dissipate any excess thermal energy generated by the cells 30 during operation.

The ICD 10 preferably uses a bank 12 of thermal cells 30 (such as from 1 to 6 cells 30 in the bank 12), wherein each battery is capable of supplying energy for a single, high energy shock. In this embodiment, the number of cells 30 in the bank 12 corresponds to the number of shocks available from the ICD 10. Upon detection of a cardiac dysryhthmia, the control and detection circuitry 16 selects an unused battery cell 30 from the bank 12 by means of switches 38 and the circuitry 16 causes that battery cell 30 to discharge its power into the converter 18 for purposes of charging capacitor system 20.

In an alternative embodiment, each cell is constructed to have an operational life of 3–4 minutes and can deliver a limited number (3–5) shocks during that period. In this embodiment, the ICD has a capacity of 10 to fifteen countershocks. It will be apparent that the selection of the number of cells 30 and operational life and output characteristics of each cell 30 can be varied to provide for different numbers of total shocks available form the ICD 10. In its intended application, once the ICD has delivered a countershock therapy once or a small number of times, it is intended to be replaced by a larger device having a higher shock capacity. For the large number of patients who never or rarely get a shock, the ICD of the present invention has the advantage of a smaller, and less expensive device which still protects them against SCD.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention.

What is claimed is:

1. A prophylactic implantable cardioverter defibrillator (ICD) comprising:

a low power output battery;

a high power output battery bank comprising a plurality of single use battery cells, a set of switches connected to the battery cells, and an output of the battery bank connected to the battery cells and the set of switches, wherein each battery cell has a finite useful life of less than an hour when activated;

a high voltage capacitor system:

a converter connected between the battery bank output and the capacitor system;

an output switching network connected to the capacitor system and connectable to a patient for discharge of a countershock thereto; and control and detection circuitry powered by the low power output battery and operably connected to the battery bank set of switches, the converter and the output switching network, the control and detection circuitry further being connectable to the patient to receive cardiac dysrythmia detection signals therefrom and, in response to such receipt, selectively charging and discharging the capacitor system to deliver a high voltage output countershock to the patient via the output switching network.

2. The ICD of claim 1 wherein the total number of battery cells is less than twenty.

3. The ICD of claim 1 wherein the battery cells are thermal battery cells.

4. The ICD of claim 1 wherein the control and detection circuitry operates the switches to select a new battery cell for each charging of the capacitor system.

5. A prophylactic implantable cardioverter defibrillator (ICD) comprising:

a low power output battery;

a high power output battery bank comprising at least one thermal battery cell having a finite useful life of less than an hour when activated;

a high voltage capacitor system;

a converter connected between the battery bank and the capacitor system;

an output switching network connected to the capacitor system and connectable to a patient for discharge of a countershock thereto; and control and detection circuitry powered by the low power output battery and operably connected to the battery bank, the converter and the output switching network, the control and detection circuitry further being connectable to the patient to receive cardiac dysrythmia detection signals therefrom and, in response to such receipt, selectively charging and discharging the capacitor system to deliver a high voltage output countershock to the patient via the output switching network.

6. The ICD of claim 5 wherein the battery bank comprises multiple thermal battery cells and further includes a set of switches connected to the battery cells and a battery bank output, the battery bank output being connected to the battery cells, the set of switches and to the converter.

7. The ICD of claim 5 wherein the control and detection circuitry operates the switches to select a new battery cell for each charging of the capacitor system.

* * * * *